ent Number: 4,508,634

Date of Patent: Apr. 2, 1985

[54] AQUEOUS SKIN CLEANER COMPOSITION COMPRISING PROPYLENE CARBONATE

[75] Inventors: Normita P. Elepaño, St. Paul, Minn.; William H. Schnur, Balsam Lake, Wis.; Jens L. Jorgensen, Ham Lake, Minn.

[73] Assignee: Minnesota Mining and Manufacturing Company, St. Paul, Minn.

[21] Appl. No.: 551,880

[22] Filed: Nov. 15, 1983

[51] Int. Cl.³ .......................... B08B 3/08; C09D 9/02; C11D 7/50; C23G 5/02
[52] U.S. Cl. .................................... 252/163; 252/162; 252/DIG. 5; 252/DIG. 8; 134/38
[58] Field of Search ................... 252/DIG. 5, DIG. 8, 252/162, 163; 134/38

[56] References Cited

U.S. PATENT DOCUMENTS

| | | | |
|---|---|---|---|
| 1,146,854 | 7/1915 | Ellis | 252/DIG. 8 X |
| 2,344,268 | 3/1944 | Rench | 252/163 X |
| 2,383,114 | 7/1945 | Villiers | 252/DIG. 5 X |
| 2,392,779 | 1/1946 | Showalter | 252/DIG. 5 X |
| 3,277,013 | 10/1966 | Gianladis | 252/153 |
| 3,382,181 | 5/1968 | Oberdorfer, Jr. | 252/170 |
| 3,541,010 | 11/1970 | Dingman et al. | 252/3 |
| 3,645,904 | 2/1972 | Beach | 252/89 |
| 4,017,615 | 4/1977 | Shastri et al. | 424/241 |
| 4,083,956 | 4/1978 | Shelton | 424/66 |
| 4,085,059 | 4/1978 | Smith et al. | 134/38 X |
| 4,120,810 | 10/1978 | Palmer | 252/163 X |

FOREIGN PATENT DOCUMENTS 0842866  7/1960  United Kingdom ......... 252/DIG. 5

OTHER PUBLICATIONS

Chemical Abstracts, vol. 91, 1979, 91:41200n.
Chemical Abstracts, vol. 96, 1982, 96:183225b.

*Primary Examiner*—John E. Kittle
*Assistant Examiner*—Mukund J. Shah
*Attorney, Agent, or Firm*—Donald M. Sell; James A. Smith; David L. Weinstein

[57]  ABSTRACT

Composition suitable for removing paint, grease, dirt and other foreign materials from the skin. The composition comprises propylene carbonate, water, at least one organic cosolvent, at least one thickening agent, at least one neutralizing agent, and at least one surfactant. In a preferred embodiment, the composition further includes a mild abrasive, wood flour, to promote the cleaning action of the propylene carbonate.

4 Claims, No Drawings

AQUEOUS SKIN CLEANER COMPOSITION COMPRISING PROPYLENE CARBONATE

BACKGROUND OF THE INVENTION

The present invention relates to cleaning compositions, and, in particular, to a cleaning composition useful for removing paint from the skin.

Although many commercially available cleaning compositions have been found to be somewhat effective in removing undried paint, greases, oils, and latex-based paints from the skin, as yet, none have been found to be effective for removing dried automotive paints and primers from the skin. Two examples of skin cleaning compositions in the patent literature are U.S. Pat. Nos. 3,277,013 and 3,645,904. U.S. Pat. No. 3,277,013 discloses a waterless skin cleaner comprising a liquid paraffinic hydrocarbon solvent, a nonionic polyethylene oxide reaction product emulsifying agent, and a synthetic hydrophilic acid polymer colloid at least partially neutralized in situ by an alkaline agent. U.S. Pat. No. 3,645,904 discloses skin cleaning compositions which contain finely comminuted plastic synthetic resin scrubber particles. The particles are intended to impart a scrubbing or mechanical detersive action to the cleaning compositions.

Painters in automotive paint and body repair shops frequently employ lacquer thinner or enamel reducer to remove automotive paints and primers from their hands. Thereupon, they wash their hands with ordinary soap and water to remove the lacquer thinner. This cleaning process renders the skin extremely dry and often leads to chapping. Although hand creams or lotions can be applied later to condition the hands and to prevent excessive dryness, chapping and drying still occur, resulting in a rough, hard skin surface.

It is known that propylene carbonate is only moderately effective as a solvent for paint, varnishes, adhesives, plastics, epoxies, and mastic compounds. Also, as a cleaning compound, it suffers from the shortcoming of instability in aqueous solutions. Only up to about 8 grams of water per 100 grams of propylene carbonate can be tolerated in water/propylene carbonate mixture. Greater amounts of water will bring about decomposition of propylene carbonate. Acids, bases, or salts present in an aqueous solution of propylene carbonate, will normally cause decomposition to occur, the primary products of which are propylene oxide and carbon dioxide.

SUMMARY OF THE INVENTION

This invention involves a composition suitable for removing paint from skin. The composition comprises propylene carbonate in an amount effective to remove dried paint from skin, at least one organic cosolvent in an amount sufficient to dissolve or disperse the effective amount of propylene carbonate and maintain a storage stable condition, at least one thickening agent to substantially prevent coagulation and demulsification of the composition, at least one buffering agent to maintain a pH in said composition so that it will be suitable for use on skin, at least one surfactant, and water to act as a vehicle for the foregoing ingredients. The composition can also include other additives which are typically found in some skin cleaning formulations, such as, moisturizers, emollients, and abrasives. In a preferred embodiment of the invention, a mild abrasive, e.g., wood flour, a fine form of sawdust, is included in the composition. In addition to providing mechanical detersive action, wood flour also promotes the cleaning action of propylene carbonate.

The composition exhibits high stability for long periods of time and is particularly useful for removing refinishing paints, e.g., acrylic lacquer, acrylic enamel, from skin. The composition removes paint from skin faster than do compositions currently available commercially. In addition, the composition is non-flammable, environmentally and toxicologically safe, and, when emollients are included, the composition reduces the dryness of the skin.

DETAILED DESCRIPTION

Propylene carbonate, sometimes referred to as a cyclic carbonate inner ester, which is useful in the composition of this invention has the formula:

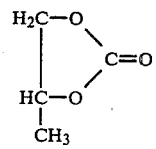

Propylene carbonate has a softening and swelling effect on paint. It can penetrate a paint film and then dissolve it so that it can be removed. Furthermore, because of its high vapor pressure, it will not rapidly evaporate and will remain on the skin and paint surface long enough to insure softening and dissolution of the paint film. Other cyclic carbonate inner esters, e.g., ethylene carbonate, may provide the necessary cleaning action, but they are not suitable in a skin cleaning composition because of toxicity, flammability, volatility, or excessive solubility in water. Excessive solubility in water renders a cyclic carbonate inner ester useless as a cleaning agent.

Water acts as a vehicle for solvents, surfactants, abrasives, and emollients, if any, as well as facilitating water rinseability. It is desirable to have a high concentration of water in the composition in order to reduce flammability and costs. Although it would be expected that the concentration of water would be no higher than 8% by weight based on the weight of propylene carbonate, the use of surfactants, to be described hereinafter, allows the incorporation of a high concentration of water, e.g., as high as 140% or more by weight, based on the weight of propylene carbonate, in the composition.

Propylene carbonate, by itself, does not easily remove the dried paint film. In addition to propylene carbonate, the composition can contain other solvents, for example, A. Monohydric alcohols having from 1 to 22 carbon atoms, such as methanol, ethanol, propanol, isopropanol, butanol, hexanol, cetyl alcohol, stearyl alcohol, and the like.

B. Dihydric and polyhydric alcohols having from 2 to 22 carbon atoms, such as propylene glycol, glycerin, hexanetriols such as 1,2,6-hexanetriol, sorbitol, 1,3-butanediol, 2,3-butanediol, etc.

C. Polyethylene glycols and polypropylene glycols having molecular weights of from 100 to 20,000.

D. Esters of aliphatic monobasic and dibasic acids having from 2 to 22 carbon atoms and monohydric alcohols having from 1 to 20 carbon atoms, di- and polyhydric alcohols having from 2 to 20 carbon atoms, and sugar alcohols such as isopropyl myristate, myristyl myristate, cetyl stearate, methyl stearate, isopropyl sebacate, methyl sebacate, sucrose monolaurate, sucrose monosteatate, etc.

These cosolvents aid in removing dried paint, stabilizing the composition, and moisturizing the skin. The cosolvents used with propylene carbonate preferably should be non-flammable and non-toxic.

Surfactants act to emulsify and wet the surface of the paint and to promote water rinseability. The surfactants suitable for the practice of the present invention must provide the proper emulsion stability, and they must be non-toxic. Representative surfactants which are suitable for the present invention include A. Anionic agents
 1. Sodium, potassium and ammonium soaps derived from fatty acids having from 10 to 22 carbon atoms.
 2. Amine soaps derived from fatty acids having from 10 to 22 carbon atoms and primary, secondary and tertiary amines such as monoethanolamine, diethanolamine and triethanolamine, and cyclic amines such as morpholine, e.g., triethanolamine stearate.
 3. Rosin soaps such as sodium salts of rosin acids such as abietic acid.
 4. Alkali metal salts of sulfate compounds which can be represented by the formula $ROSO_3H$ wherein the R group represents an organic moiety such as a fatty alcohol having up to 22 carbon atoms. These include sodium lauryl sulfate, sodium cetyl sulfate, sodium monolauryl glyceryl sulfate, an oil such as sulfated castor, olive, teaseed, neat's foot cottonseed, rape seed, corn and rice, oil, etc.
 5. Alkali metal salts of sulfonated compounds which can be represented by the formula $RSO_3H$ wherein the R group represents an organic moiety having from 8 to 22 carbon atoms. These include alkane sulfonates such as dioctyl sodium sulfosuccinate, oxyethylated alkyl lauryl sulfate, alkyl aromatic sulfonates such as sodium isopropylnaphthalenesulfonate, sodium dodecylbenzenesulfonate, sodium sulfonaphthylstearate.

B. Cationic agents
 1. Amine salts (e.g. hydrochlorides and acetates) derived from straight chain fatty amines having from 8 to 18 carbon atoms, e.g., octyldecylamine hydrochloride.
 2. Quaternary ammonium salts formed by alkylation of fatty amines with methyl chloride, dimethylsulfate, benzylchloride and the like. These compounds can be represented by the formula $[RR'R''R''']NY$ wherein each of R, R', R'', R''' is a long chain aliphatic group of from 8 to 22 carbon atoms or a fatty acid amide; short aliphatic group such as methyl, ethyl, or propyl, an aromatic group such as a phenyl or benzyl radical; or a heterocyclic group such as pyridine or piperidine; and Y represents an inorganic or lower organic ion such as chloride, bromide or acetate radical, e.g., triethanolamine stearate, cetyl trimethyl ammonium bromide, benzylalkonium chloride.

C. Nonionic agents
 1. Ethers such as condensation products of alkylphenols with from 6 to 20 moles of ethylene oxide, the phenols being monoalkylated, dialkylated or polyalkylated with alkyl side chains having from 5 to 18 carbon atoms and the corresponding naphthalene or diphenyl compounds; polyoxyethylene and polyoxyethylene-polyoxypropylene copolymers.
 2. Esters such as compounds which can be represented by the formula RCOOR' wherein R is a long hydrocarbon chain derived from a fatty acid having from 12 to 22 carbon atoms and R' is a polyhydric alcohol, e.g., glyceryl monostearate, diethylene glycol monolaurate, sorbitan fatty acid eters derived, for example from lauric, palmitic, stearic and oleic acids.
 3. Ether-esters wherein polyoxyethylene chains are found with an unreacted hydroxy group of esters of fatty acids and polyhydric alcohols.
 4. Fatty acid amides such as lauroyl diethanolamide.

D. Ampholytic
 1. Surfactants such as those having amino and carboxy groups, e.g., dodecyl $\beta$-alanine, imidazoline derivatives.
 2. Surfactants containing amino and sulfuric acid or sulfonic groups formed by condensing an alkanesulfonamide with formaldehyde and methyltaurine.

Suitable representative surfactants include sorbitan trioleate, sorbitan tristearate, sorbitan sesquioleate, glycerol monostearate, sorbitan monostearate, sorbitan monopalmitate, sorbitan monolaurate, polyoxyethylene lauryl ether, polyethylene glycol monostearate, triethanolamine oleate, polyoxyethylene glycol monolaurate, polyoxyethylene sorbitan monostearate, polyoxyethylenesorbitan monooleate, polyoxyethylene sorbitan monolaurate, sodium oleate, potassium oleate, sodium lauryl sulfate, lauroyl imidazoline, sodium dodecylbenzene sulfonate, sodium monoglyceride sulfate, sodium alkaralkyl polyglycol sulfate, sodium oleyl laurate, sodium dioctyl sulfosuccinate, lauryl polyglycol, ether sodium dibutylnaphthalenesulfonate, alkyl phenol polyglycol ether, sorbitan monolaurate polyglycol ether, sulfonated castor oil, tall oil polyglycol ester, alkyl dimethyl benzylammonium chloride alkyl naphthalene pyridinium chloride, cetyl dimethyl ethylammonium bromide, alkyl dimethyl chlorobenzylammonium chloride, dibutyl phenyl phenol sulfonate, ester of colaminoethylformyl methyl pyridinium chloride, sulfonated methyl oleylamide, sorbitan monolaurate polyglycol ether, polyglycol oleate, sodium lauryl sulfoacetate, sodium 2-ethylhexanol sulfate, sodium 7-ethyl-2-methylundecanol-4 sulfate, sodium 3,9-diethyltridecanol-6 sulfate, sodium lauryl and myristyl collamide sulfate and N-(sodium sulfoethyl)oleamide, etc. The preferred surfactants are fatty acid esters and fatty alcohol esters.

Thickening agents act as protective colloids, operating to prevent coagulation and demulsification of the composition. They further act to prevent coagulation of the emulsion particles which constitute the composition of the present invention.

Suitable thickening agents for use in the composition of this invention include colloidal alumina, colloidal silica, alginic acid and derivatives thereof, "Carbopol" (carboxyvinyl polymer), cellulose derivatives such as "Klucel" (cellulose ethers), "Methocel" (methyl cellulose), "Natrosol" (hydroxyethyl cellulose), sodium carboxymethyl cellulose, gelatin, gums such as agar, tragacanth, acacia gum, guar gum, and the like and egg yolk, lecithin, pectin, thixin, and resins like ethyleneoxide polymers.

The functions of the buffering agent are to maintain the composition at the desired pH in order to thicken the emulsion, to reduce irritability to the skin, and to prevent decomposition of the cyclic carbonate inner ester. The buffering agent must be non-toxic and must not upset the stability of the emulsion. The preferred buffering agent is triethanolamine, the reason being that it is volatile. Other buffering agents suitable in the practice of the present invention include alkali metal hydroxides, e.g. sodium hydroxide and potassium hydroxide, ammonium hydroxide, and water soluble amines, e.g., ethyl amine, diethyl amine.

Moisturizers and emollients can be included in the composition to prevent drying and chapping of the skin. Moisturizers and emollients are preferably selected from petrolatum and mineral oil because of their availability and low cost. Products derived from lanolin can also be used.

Petrolatum components useful in the practice of this invention can be any paraffinic hydrocarbon ranging in viscosity from that of mineral oil to that of paraffin waxes. The preferred petrolatums are paraffinic hydrocarbons having the consistency of petrolatum NF (petroleum jelly) and mineral oil.

Other additives are well known in the art and include preservatives, e.g., methyl paraben, propyl paraben, and the like, abrasives, e.g. wood flour, glass bubbles, sand, volcanic ash, ground cork, ground corn cobs, polymeric particles, clays, silicas, and the like; diluents, e.g., isoparaffinic hydrocarbons (Isopar L, Exxon Corp).

Compositions of the present invention can be prepared by the following method:

A. The water, thickening agents, surfactants, preservatives, cyclic carbonate inner ester, and cosolvents are introduced into a vessel. The resulting mixture is stirred while the temperature of the composition is brought to about 50° C. in order to minimize thermal stock when the mixture containing the remaining ingredients are added to the mixture containing the cyclic carbonate inner ester;

B. The emollients, abrasives, additional cosolvents, and diluents are introduced into a second vessel. The resulting mixture is stirred while the temperature is brought to 50° C. in order to dissolve emollients in solid or gel form;

C. The mixture in B is slowly added, with stirring to the mixture in A, and the combined mixtures are cooled to 25° C.

D. The buffering agent is then added to thicken the composition.

If abrasives are not included in the composition, scrubbing or mechanical detersive action can be provided by brushes, sponges, cloths, non-woven pads, or the like after the composition has been applied to the surface of the skin. However, it has been found that the inclusion of certain abrasives, particularly cellulosic abrasives, e.g., wood flour, ground sponge, ground cork, promote the cleaning action of the propylene carbonate in the compositions of the invention.

The following table sets forth the concentration ranges of the various ingredients of compositions suitable for the practice of this invention:

TABLE I

| Ingredient | Concentration Range (parts by weight) |
| --- | --- |
| Water | 10–50 |
| Propylene carbonate | 10–40 |
| Cosolvents | 1–30 |
| Surfactants | 0.5–12 |
| Thickening agents | 0.1–5 |
| Neutralizing agents | 0.01–1.0 |
| Preservatives | 0–0.5 |
| Moisturizers/emollients | 0–25 |
| Abrasive materials | 0–15 |

The skin cleaning composition is effective for removing refinish automotive paints and primers, as well as grease and dirt. The composition has excellent chemical stability and emulsion stability as demonstrated in natural age, freeze/thaw, and 50° C. heat age tests. The composition exhibits a heat age stability value of 1400 hrs at 50° C.

In order to use the composition of this invention to remove paint, grease, dirt, and the like from skin, the user can apply the composition, in an effective amount, to the soiled area, rub the area with the hands or a mechanical scrubbing device, e.g. brushes, cloths, to penetrate the film of paint, grease, etc., and then rinse the loosened foreign substance with water.

The following non-limiting example further illustrates the invention.

EXAMPLE I

The following ingredients, in the amounts indicated, were combined to form a skin-cleaning composition:

| Ingredient | Amount (parts by weight) |
| --- | --- |
| Part A | |
| Deionized water | 34.55 |
| Propylene carbonate | 25.20 |
| Cosolvents | |
| Propylene glycol | 5.20 |
| Ethanol | 1.90 |
| Thickening agent | 0.36 |
| Polyacrylic acid polymer ("Carbopol" 940, available from B. F. Goodrich Chemical Co.) | |
| Preservative | 0.10 |
| Methyl paraben | |
| Nonionic surfactants | |
| Alkoxylated fatty alcohol ("Plurafac" D-25, available from BASF Wyandotte) | 1.30 |
| Polyoxyalkylene sorbitan monooleate ("Tween" 80, available from ICI Americas, Inc.) | 4.00 |
| Part B | |
| Emollients | |
| Mineral oil ("Carnation", available from Witco Chemical Corporation) | 7.70 |
| Petrolatum ("Protopet" White 1S, available from Witco Chemical Corporation) | 7.00 |
| Diluent | 7.60 |
| Isoparaffinic hydrocarbon ("Isopar" L, available from Exxon) | |
| Abrasive | 5.00 |
| Wood flour (available from Wilner Wood Products, Co., Norway, Maine) | |
| Part C | |
| Buffering agent | 0.074 |
| Triethanol amine | |

The ingredients of Part A were introduced into a stainless steel beaker with stirring, and the resulting mixture was heated to 50° C. The ingredients of Part B were introduced into a second stainless steel beaker with stirring, and the resulting mixture was heated to 50° C. The mixture of Part B was then slowly added to the mixture of Part A with stirring. The resulting mixture was then cooled to 25°–30° C. Part C was then added to the mixture consisting of Part A and Part B, and stirring was continued for 30 minutes. The resulting mixture was a smooth, creamy emulsion.

The foregoing composition was compared with various commercially available skin-cleaning compositions to determine effectiveness of paint removal. The apparatus for testing the effectiveness of the skin cleaner was substantially identical to that described in Jorgensen, U.S. Pat. No. 4,155,870, the disclosure of which is incorporated herein by reference.

The apparatus includes a scrubbing device powered by an air motor. The stiff plastic brush described in U.S. Pat. No. 4,155,870 was replaced with a scrubbing assembly comprising, from top to bottom, a hard rubber circular disk having a diameter of 2½ inches, an intermediate backing made of an abrasive coated vinyl polymer, and a layer of cheesecloth.

A counter is attached to the scrubbing device so that the number of revolutions of the device can be recorded. The laboratory jack described in U.S. Pat. No. 4,155,870 was replaced with a test arm which is essentially a lever, at one end of which is placed the test panel and at the other end of which is applied a counterweight (1042 g). The fulcrum is located 20 cm from the counterweight and 9.5 cm from the test panel. The procedure for testing the effectiveness of the skin cleaner was as follows:

1. A sandblast stencil was laminated to one side of a 4 in.×4 in. steel test panel and weighed to the nearest 0.01 g. The sandblast stencil was made of uncured rubber. This rubber is normally used for sand blasting granite and is referred to as "SCOTCH" Brand Sand Blast Stencil Tape #507-45BC Buttercut with a pressure-sensitive adhesive and release liner applied to one surface, (available from 3M Company, St. Paul, Minn.). This substrate is used because it is flat and flexible and has surface properties similar to human skin. The adhesive coating on one surface holds the substrate firmly in place during the test.
2. A light coat of refinish acrylic lacquer, approximately 0.20 g when dry, was painted over the panel. The sandblast stencil color showed through slightly.
3. The panel was allowed to age for one hour, re-weighed, and tested.
4. 1.5 g of the skin cleaner to be tested was evenly spread over a 2½ in. circle in the center of the test panel. The scrubbing assembly was placed in position, the cheesecloth being in contact with the test panel. The test panel was placed on one end of the test arm, and the counterweight was placed on the other end.
5. The air motor was turned on, its speed being approximately 60 rpm, and allowed to turn the number of revolutions shown in Table II. The panel was then removed, the excess material wiped off, and the performance graded as a function of paint removed from the 2½ in. circle.
6. A scale of 1–5 was set up to grade the effectiveness of each cleaner.
  1—5% of paint removed
  2—15% of paint removed
  3—25% of paint removed
  4—50% of paint removed
  5—90% of paint removed.

Table II compares the effectiveness of various commercially available skin cleaning compositions with the skin-cleaning composition of Example I. The effectiveness was measured after 15, 100, 200 and 300 cycles of the test apparatus.

TABLE II

| Product | Effectiveness | | | |
|---|---|---|---|---|
| | 15 cycles | 100 cycles | 200 cycles | 300 cycles |
| U.S. Aviex Hand Cleaner (U.S. Aviex Co., Niles, Michigan) | 0.0 | 0.0 | 0.0 | 0.0 |
| Blue Label DL Biodegradable Hand Cleaner (D.L. Skin Care Products, Buffalo, N.Y.) | 0.0 | 0.0 | 0.0 | 0.0 |
| New DL Heavy Duty Hand Cleaner with Lanolin (D.L. Group Banite, Buffalo, N.Y.) | 0.0 | 0.0 | 1.0 | 2.0 |
| "Vin-Dotco Really Works" Heavy Duty Hand Cleaner (Vin-Dotco, Inc., Clearwater, Fla.) | 2.0–2.5 | 5.0 | | |
| "Vin-Dotco Really Works" 140 Citrus Hand Cleanser (Vin-Dotco, Inc., Clearwater, Fla.) | 0.5 | 3.5 | | 5.0 |
| "Go-Jo Remove" Pumice Hand Cleaner (Go-Jo Industries, Akron, Ohio) | 0.5–1.0 | 5.0 | | |
| "Hand Kind" 266 (Polychrome Corp., Yonkers, N.Y.) | 0.5 | 4.5 | | |
| Composition of Example I | 5.0 | | | |

From the foregoing table, it can be seen that the composition of the present invention is superior to commercially available skin cleaners as a paint remover.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A composition useful for removing paint, primer grease, dirt from the surface of skin comprising:
   (a) from about 10% to about 40% by weight propylene carbonate,
   (b) from about 10% to about 50% by weight water,
   (c) from about 1% to about 30% by weight at least one cosolvent,
   (d) from about 0.5% to about 12% by weight at least one surfactant,
   (e) from about 0.1% to about 5% by weight at least one thickening agent,
   (f) from about 0.01% to about 1% by weight at least one buffering agent, and
   (g) from 0% to about 15% by weight at least one abrasive material.

2. The composition of claim 1 wherein said at least one abrasive material is wood flour.

3. The composition of claim 1 further including at least one emollient.

4. A method for removing paint, primer, grease, dirt from the skin comprising rubbing the skin with an effective amount of the skin cleaning composition of claim 1.

* * * * *